(12) United States Patent
Modglin

(10) Patent No.: US 9,011,357 B2
(45) Date of Patent: Apr. 21, 2015

(54) CERVICAL COLLAR WITH CABLE ADJUSTMENT SYSTEM

(71) Applicant: DeRoyal Industries, Inc., Powell, TN (US)

(72) Inventor: Michael D. Modglin, Braselton, GA (US)

(73) Assignee: DeRoyal Industries, Inc., Powell, TN (US)

( * ) Notice: Subject to any disclaimer, the term of this patent is extended or adjusted under 35 U.S.C. 154(b) by 0 days.

(21) Appl. No.: 14/132,323

(22) Filed: Dec. 18, 2013

(65) Prior Publication Data
US 2014/0107551 A1     Apr. 17, 2014

Related U.S. Application Data

(60) Continuation-in-part of application No. 13/780,165, filed on Feb. 28, 2013, now Pat. No. 8,721,576, and a division of application No. 13/226,151, filed on Sep. 6, 2011, now Pat. No. 8,449,485.

(51) Int. Cl.
*A61F 5/00* (2006.01)
*A61F 5/055* (2006.01)

(52) U.S. Cl.
CPC ..................... *A61F 5/055* (2013.01)

(58) Field of Classification Search
USPC ............................... 602/17–19; 128/DIG. 23
See application file for complete search history.

(56) References Cited

U.S. PATENT DOCUMENTS

| | | | |
|---|---|---|---|
| 4,968 A | 2/1847 | Knapp |
| 197,243 A | 11/1877 | Boylston |
| 1,930,440 A | 10/1933 | Longfellow |
| 2,474,200 A | 6/1949 | McBee |
| 2,791,999 A | 5/1957 | Bustamante |
| 3,042,027 A | 7/1962 | Monfardini |
| 3,521,057 A | 7/1970 | Morlan |
| 3,596,655 A | 8/1971 | Corcoran |
| 4,888,831 A | 12/1989 | Oleson |
| 5,005,563 A | 4/1991 | Veale |
| 5,180,361 A | 1/1993 | Moore et al. |

(Continued)

FOREIGN PATENT DOCUMENTS

| | | |
|---|---|---|
| ES | 2237303 A1 | 8/2003 |
| FR | 2704424 | 4/1993 |

(Continued)

OTHER PUBLICATIONS

International Search Report, PCT/US2012/051281, date of mailing Dec. 24, 2012 (18 pages).

(Continued)

*Primary Examiner* — Michael A. Brown
(74) *Attorney, Agent, or Firm* — Luedeka Neely Group, PC

(57) ABSTRACT

A cervical collar having a vertically adjustable chin support, the collar including chin support adjustably connected to a collar body having a stop guide, an adjustment member for adjusting the length of a cable trained around a pulley located on the collar body adjacent to the cable guide and connected to a cable stop connecting between the collar body and the chin support and movably positionable along the stop guide on the collar body, wherein the length of the cable adjusts the position of the cable stop along the stop guide and adjusts the vertical position of the chin support relative to the collar body.

7 Claims, 15 Drawing Sheets

(56) References Cited

U.S. PATENT DOCUMENTS

| | | |
|---|---|---|
| 5,302,170 A | 4/1994 | Tweardy |
| 5,688,229 A | 11/1997 | Bauer |
| 5,865,773 A | 2/1999 | Koledin |
| 5,993,403 A | 11/1999 | Martin |
| 6,315,746 B1 | 11/2001 | Garth et al. |
| 6,423,020 B1 | 7/2002 | Koledin |
| 6,503,213 B2 | 1/2003 | Bonutti |
| 6,599,257 B2 | 7/2003 | Al-Obaidi et al. |
| 6,770,047 B2 | 8/2004 | Bonutti |
| 7,120,954 B2 | 10/2006 | Traut et al. |
| 7,128,724 B2 | 10/2006 | Marsh |
| 7,297,127 B2 | 11/2007 | Lee et al. |
| 7,371,222 B2 | 5/2008 | Heinz et al. |
| 7,674,234 B2 | 3/2010 | Calco et al. |
| 7,806,842 B2 | 10/2010 | Stevenson et al. |
| 7,954,204 B2 | 6/2011 | Hammerslag et al. |
| 7,992,261 B2 | 8/2011 | Hammerslag et al. |
| 8,251,934 B2 | 8/2012 | Bonutti |
| 2004/0204666 A1 | 10/2004 | Marsh |
| 2005/0113728 A1 | 5/2005 | Heinz et al. |
| 2006/0135897 A1 | 6/2006 | Dellanno |
| 2007/0027418 A1 | 2/2007 | Calco et al. |
| 2008/0066272 A1 | 3/2008 | Hammerslag et al. |
| 2008/0091132 A1 | 4/2008 | Bonutti |
| 2009/0149788 A1 | 6/2009 | Dellanno |
| 2009/0287128 A1 | 11/2009 | Ingimundarson et al. |
| 2010/0268139 A1 | 10/2010 | Garth |

FOREIGN PATENT DOCUMENTS

| | | |
|---|---|---|
| GB | 862277 | 3/1961 |
| GB | 1132607 | 11/1968 |
| GB | 1290523 | 9/1972 |
| GB | 2194156 A | 3/1988 |
| GB | 2233900 A | 1/1991 |
| JP | 0326251 | 2/1991 |
| JP | 0721013 | 7/1995 |

OTHER PUBLICATIONS

J.H. Willard from Brownhelm, Ohio, U.S.A. Fracture Apparatus, Patented Jun. 11, 1836, U.S. Patent No. Unknown 9720X.

Frontier Medical New Zealand Ltd, 4 Fisher Crescent, Mt. Wellington, Auckland, New Zealand Ferno Wizloc Cervical Collar—Military Spec FW-WLG Copyright 2008 www.frontmed.co.nz.

Dellano of Bloomfield, New Jersey, U.S.A. Forward Head Posture Correction Collar U.S. Appl. No. 60/638,061, filed Dec. 21, 2001.

Japanese Patent No. JPH0284614U No Translation Available, 1990.

CERVICAL COLLAR WITH CABLE ADJUSTMENT SYSTEM

CROSS-REFERENCE TO RELATED APPLICATIONS

This application is a continuation-in-part application of co-pending U.S. application Ser. No. 13/780,165, filed Feb. 28, 2013, and entitled CERVICAL COLLAR WITH CABLE REEL ADJUSTMENT SYSTEM, which is a divisional application of U.S. application Ser. No. 13/226,151, filed Sep. 6, 2011, now U.S. Pat. No. 8,449,485, issued May 28, 2013, and entitled CERVICAL COLLAR WITH CABLE REEL ADJUSTMENT SYSTEM, each incorporated by reference herein in their entireties.

FIELD

This disclosure relates to the field of size adjustable cervical collars. More particularly, the disclosure relates to cervical collars that enable improved adjustment of the height of the chin support.

BACKGROUND

Cervical collars are used to maintain the spine of a patient in a desired orientation by immobilizing the neck of the patient and supporting the chin at a desired, generally level or neutral position. The position of the chin is maintained by locating a chin support to contact and support the underside of the chin at a desired angle.

The expense of cervical collars has resulted in various forms of adjustable collars that enable a single collar model to be used for a variety of patient sizes. However, a desire for improvement in the construction of adjustable collars remains.

SUMMARY

The disclosure relates to a cervical collar having a vertically adjustable chin support. In one aspect, the collar includes a chin support adjustably connected to a collar body having a stop guide, an adjustment member for adjusting the length of a cable trained around a pulley located on the collar body adjacent to the cable guide and connected to a cable stop connecting between the collar body and the chin support and movably positionable along the stop guide on the collar body. The length of the cable adjusts the position of the cable stop along the stop guide and adjusts the vertical position of the chin support relative to the collar body.

In another aspect, the collar includes chin support adjustably connected to a collar body configured to be positioned adjacent a neck of a patient and defining a stop guide, a cable having a portion connected to an adjustment member adjustably positionable relative to the collar body for selectively adjusting the length of the cable, and a cable stop connecting between the collar body and the chin support and movably positionable along the stop guide on the collar body and a pulley located on the collar body adjacent to the elongate slot. A distal portion of the cable is connected to the cable stop and the cable is trained about the pulley so that the direction of the cable is changed between the cable stop and the adjustment member, and adjustment of the length of the cable adjusts the position of the cable stop along the stop guide and adjusts the vertical position of the chin support relative to the collar body.

In yet another aspect, a cervical collar having a vertically adjustable chin support, includes a rear collar portion and a front collar assembly. The front assembly includes a chin support positionable at the front of a user with the chin of the user resting in the chin support. The rear collar portion is positionable at the back of the user, with the front collar assembly and the rear collar adjustably secured together to fit the neck of the user to restrain movement of the neck. The front assembly also includes a main collar body connected to the chin support and an adjustable collar body connected to the main collar body, the adjustable collar body including a stop guide defined thereon, a cable having a portion connected to an adjustment member adjustably positionable on the adjustable collar body for selectively adjusting the length of the cable, and a cable stop movably positionable along the stop guide and connected to the main collar body, and a pulley located on the collar body adjacent to the stop guide. A distal portion of the cable is connected to the cable stop and the cable is trained about the pulley so that the direction of the cable is changed between the cable stop and the adjustment member, and adjustment of the length of the cable adjusts the position of the cable stop along the slot and adjusts the vertical position of the chin support relative to the collar body.

In a still further aspect, a cervical collar having a vertically adjustable chin support includes a chin support adjustably connected to a collar body configured to be positioned adjacent a neck of a patient and defining a stop guide, a cable having a portion connected to an adjustment member adjustably positionable relative to the collar body for selectively adjusting the length of the cable, and a cable stop connecting between the collar body and the chin support and movably positionable along the stop guide on the collar body. Adjustment of the length of the cable by adjusting the position of the adjustment of the adjustment member relative to the collar body adjusts the position of the cable stop along the stop guide and adjusts the vertical position of the chin support relative to the collar body.

BRIEF DESCRIPTION OF THE DRAWINGS

Further advantages of the disclosure are apparent by reference to the detailed description when considered in conjunction with the figures, which are not to scale so as to more clearly show the details, wherein like reference numbers indicate like elements throughout the several views, and wherein.

DETAILED DESCRIPTION

The disclosure relates to an adjustable body support. The body support may be configured to adjustably support the chin of a user, or other anatomical portions of a patient.

Figure 15:
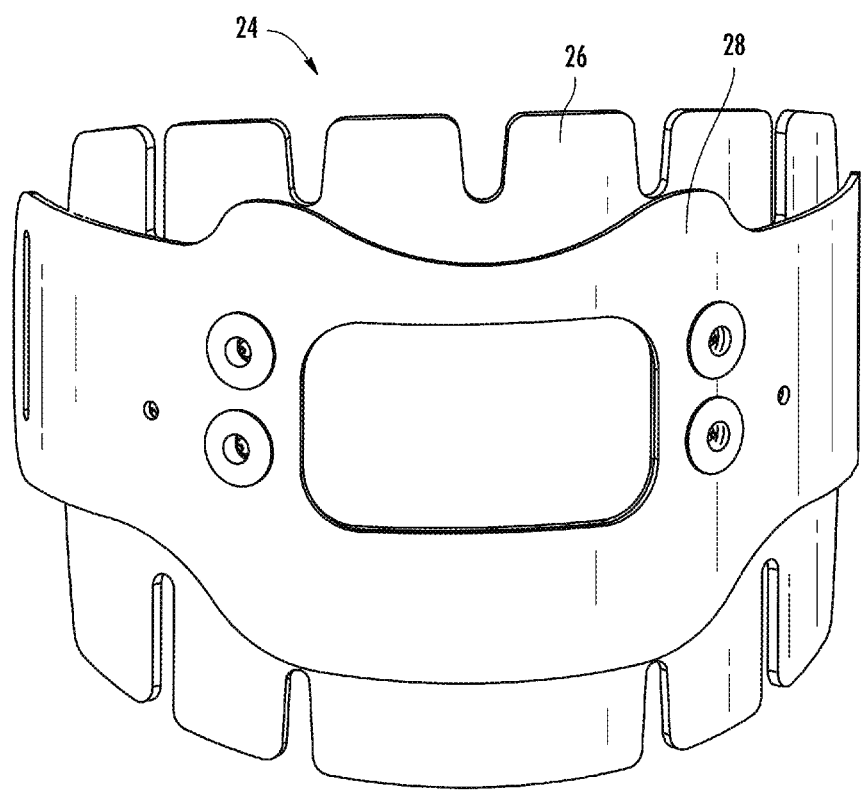
FIG. 15 shows a back assembly of a cervical collar for use with the front assembly of FIG. 1 to provide a cervical collar according to the disclosure.

With reference to the drawings, in one embodiment, the body support is a cervical collar 10 configured to enable adjustment of the height of a chin support 12 of the collar 10. The collar 10 also includes an adjustable front assembly having a front main body 14 having body portions 14a and 14b, front a front adjustable body 16 having adjustable body portions 16a and 16b, cable positioning systems 18a and 18b, and a cable adjustment system 20 or a cable adjustment system 20' or both. The front assembly may also include a sternal pad 22. The collar 10 also includes a rear assembly 24 having an occipital support 26 and a posterior support 28 (FIG. 15).

The cervical collar 10 is positioned about the neck of a user with the front assembly 14 situated at the front of the user with the chin of the user resting in the chin support 12, and the rear assembly 24 at the back of the user. The front assembly 14 and the rear assembly 24 are adjustably secured together as by straps to comfortably but snugly fit the neck of the user to restrain movement of the neck. The front assembly 14 is adjusted to situate the chin support 12 to maintain the chin of the user at a desired orientation, typically level.

The chin support 12 is of one-piece molded plastic construction, such as low density polyethylene) and is characterized as having a central located u-shaped portion 12a, with adjacent side wings 12b and 12c on either side of the u-shaped portion 12a. The u-shaped portion 12a is suitably shaped to receive the chin of a user for supporting the chin and may include padding or the like for additional comfort of the user if desired. The chin support 12 is mounted to front main body 14 as by plastic rivets.

The front main body 14 is of one-piece molded plastic construction and is characterized as having a central connector 14a bridging between adjacent side wings 14b and 14c. The connector 14a spans between upper portions of the side wings 14b and 14c to define a cut-out for providing clearance for a tracheal tube of the like. The wings 14b and 14c include elongate, and preferably curved, slots 30a and 30b, respectively. The slots 30a and 30b receive connectors 32a and 32b, respectively, fixedly located on the adjustable body portions 16a and 16b. The connectors 32a and 32b may be, for example, projections sized to extend through the slots 32a and 32b with a head or the like on the distal ends thereof for maintaining the connectors 32a and 32b within the slots 30a and 30b. In this regard, it will be observed that the lowermost end of each of the slots 30a and 30b has an enlarged or bulbous portion to permit passage of the heads of the connectors 32a and 32b for installation. Thus, the slots 30a and 30b cooperate with the connectors 32a and 32b to guide movement of the front adjustable body 16 relative to the main body 14.

The chin support 12 and the main body 14 may be provided as a unitary piece; however, having them as separate portions enables better conformity to the anatomy of the patient. Also, the adjustable body portions 16a and 16b may be provided as a single body portion, but, are preferably provided as two pieces that pivotally connect as described herein for improved conformity to the patient throughout the range of the height adjustment of the chin support 12.

The adjustable body portion 16a is of one-piece molded plastic construction and is configured to overlie about one-half of the sterna or upper chest region of the patient. The adjustable body portion 16b is substantially a mirror image of the body portion 16b for overlying the other about one-half of the sterna or upper chest region of the patient. The body portions 16a and 16b overlap at their lowermost portions and pivotally attach to one another as by a fastener, ribbed projection, rivet, or the like extending through aligned apertures 34a and 34b thereof. For example, the sternal pad 22 may include a ribbed projection 36 that extends through the apertures 34a and 34b and which is retained by a snap washer 38.

The body portion 16a includes a slot 40a adjacent a distal or raised end thereof, and the body portion 16b includes a slot 40b adjacent a distal or raised end thereof. The slots 40a and 40b receive connectors 42a and 42b, respectively, fixedly located on the adjustable body portions 16a and 16b. The connectors 42a and 42b may be, for example, projections sized to extend through the slots 40a and 40b with a head or the like on the distal ends thereof for maintaining the connectors 42a and 42b within the slots 40a and 40b. Thus, the slots 40a and 40b cooperate with the connectors 42a and 42b to guide movement of the front adjustable body 16 relative to the main body 14.

The cable positioning system 18a is located on the exterior of the body portion 16a and includes a cable guide 50a, a pulley 52a, a cable stop Ma, and a stop guide 56a defined on the body portion 16a. The cable positioning system 18b is substantially identical to the cable positioning system 18a and is located on the exterior of the body portion 16b, and includes a cable guide 50b, a pulley 52b, a cable stop 54b, and a stop guide 56b. For the sake of brevity, the positioning system 18a is described below, it being understood that the positioning system 18b and the cable guide 50b, pulley 52b, cable stop 54b, and stop guide 56b are correspondingly configured.

The cable guide 50a may be a channel or chase or the like molded or otherwise provided on the body portion 16a having a generally vertical orientation so as to be able to guide a cable, such as a cable 60, from a lower portion of the body portion 16a to an upper portion of the body portion 16a. The pulley 52a provides a structure that changes the direction of the cable 60 trained over it. Thus, as shown, the pulley 52a may be provided as by a J-shaped portion of the cable guide 50a configured to bend the cable 60 back toward a lower portion of the body portion 16a.

The cable stop 54a is a plastic knob or the like that is configured to include a cable receiver 62a, such as a through bore, for receiving one end of the cable 60, and configured to be guided by the stop guide 56a. For example, in the described embodiment, the stop guide 56a is provided by a generally vertical slot defined through the body portion 16a, and the cable stop 54a is configured to slidingly engage the stop guide 56a. To accomplish this, the cable stop 54a includes a front surface 64a wider than the slot of the stop guide 56a, a middle portion 66a sized to be received by the slot of the stop guide 56a, and a rear surface 68a wider than the slot of the stop guide 56a, such that the middle portion 66a of the cable stop 54a is captured in the slot of the stop guide 56a. The receiver 62a of the cable stop 54a may be formed in the middle portion 66a of the cable stop 54a.

The cable stop 54a is also configured to be fixed to the body portion 14 for enabling movement of the main body portion 14 relative to the adjustable body portion 16a. In this regard, a ribbed projection 70a extends from the rear surface 68a of the cable stop 54a and projects through a corresponding aperture 72a of the body portion 14. The projection 70a is captured by a plastic washer 74a or the like to connect the main body portion 14 and the adjustable body portion 16a, with the main body portion 14 being able to move relative to the adjustable body portion 16a commensurate with the stop guide 56a. The cable stop 54b is situated in the same manner and projects through a corresponding aperture 72b of the body portion 14 and captured by a plastic washer 74b or the like to connect the main body portion 14 and the adjustable body portion 16b, with the main body portion 14 being able to move relative to the adjustable body portion 16b commensurate with the stop guide 56b.

The cable adjustment system 20 is configured to include an adjustment member 80 configured to engage a portion of the cable 60, such as the midpoint M of the cable 60, and adjustably fix its position relative to a fixed location on the cervical collar 10. In this manner, the positions of the cable stops 54a and 54b may be adjusted to enable adjustment of the vertical position of the chin support 12 by vertically adjusting the vertical position of the main body portion 14 relative to the adjustable body portions 16a and 16b. As will be appreciated, by moving the midpoint M, the cable stops 54a and 54b may be moved yet remain substantially level relative to one another. In this regard, it will also be appreciated that the cable 60 may be provided in two separate segments, with each segment connected to the adjustment member 80, or a separate adjustment member provided for each cable segment.

In a preferred embodiment, the fixed location on the cervical collar 10 relative to which the midpoint M of the cable 60 is adjustably positioned is a location on the sternal pad 22. The adjustment member 80 may be a strip of flexible material including loop/hook material 82 therewith cooperatively arranged with the sternal pad 22 to enable selective positioning of the midpoint M of the cable 60 relative to the sterna pad 22. For example, the cable 60 may be threaded through a passage of the adjustment member 80 at one end thereof, and the remainder of the adjustment member 80 threaded through apertures 22a and 22b of the sterna pad 22. The hook/loop material of the adjustment member 80 may cooperate with loop/hook material 82 provided on the sterna pad 22 and/or loop/hook material of the adjustment member 80 so as to enable adjustable fixation of the adjustment member 80, and hence the location of the midpoint M of the cable relative to the sterna pad 22. For centralization of the location of the midpoint M on the sternal pad 22 and to provide a surrounding enclosure, a ring 84 may be provided on the sternal pad 22, with the ring 84 including an aperture at its lower portion for passage of the adjustment member 80.

The chin support 12 is fixedly mounted to the main body portion 14 as by mutually aligned apertures and plastic fasteners. Thus, as the main body portion 14 is vertically adjusted using the tensioning systems 18a and 18b, the chin support 12 is likewise vertically adjusted relative to the relative to the positions of the body portions 16a and 16b. By utilizing the cable adjustment system 20 to adjust the position of the midpoint M of the cable, the cable positioning systems 18a and 18b are utilized to vertically adjust the position of the chin support 12 relative to the body portions 16a and 16b which remain substantially statically positioned around the neck of the user.

Figure 1:
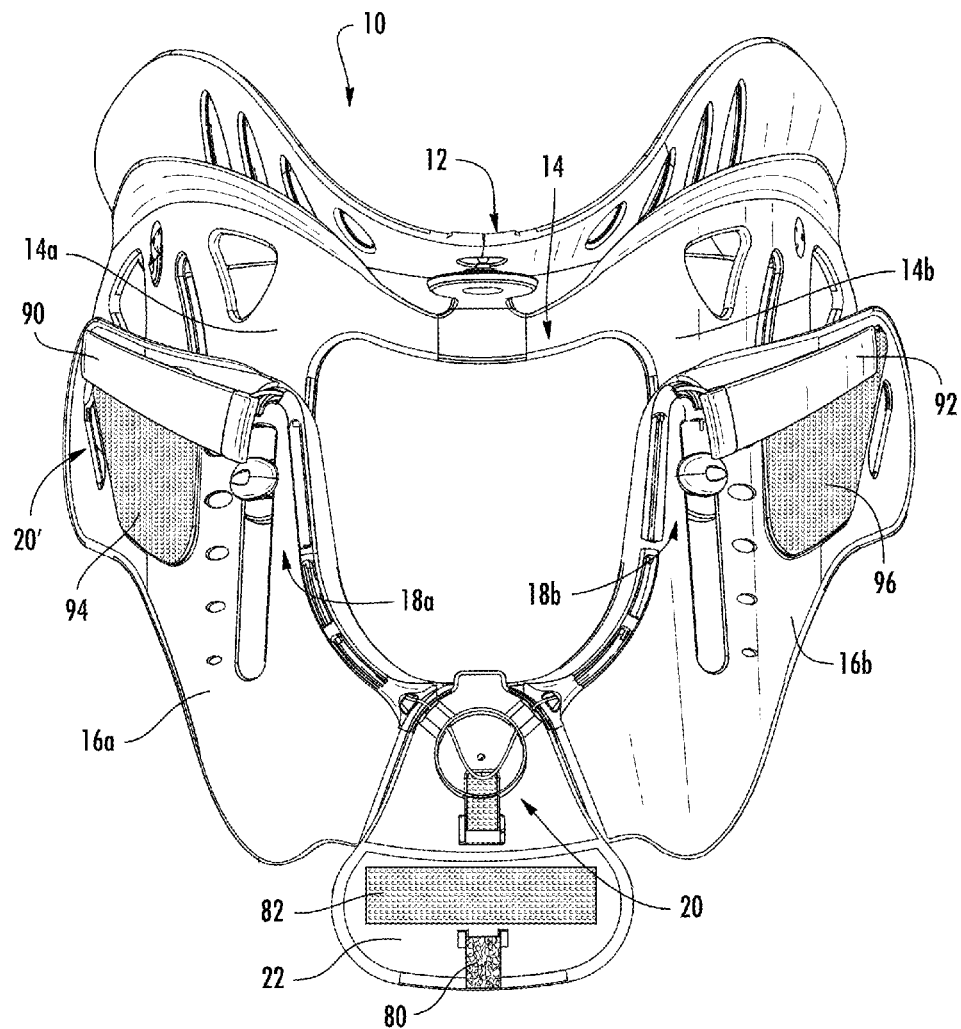
FIG. 1 is a front view of a front assembly for a cervical collar according to the disclosure.
Figure 2:
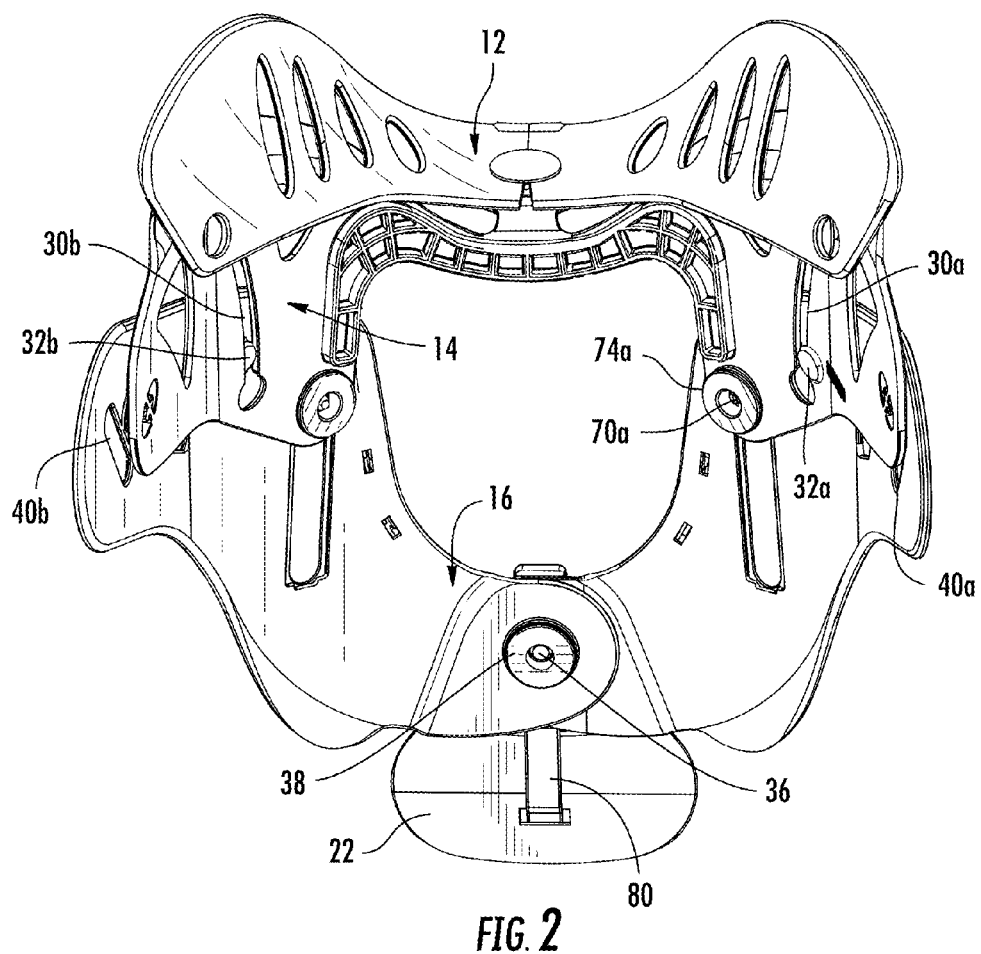
FIG. 2 is a rear view of the front assembly of FIG. 1.
Figure 3:
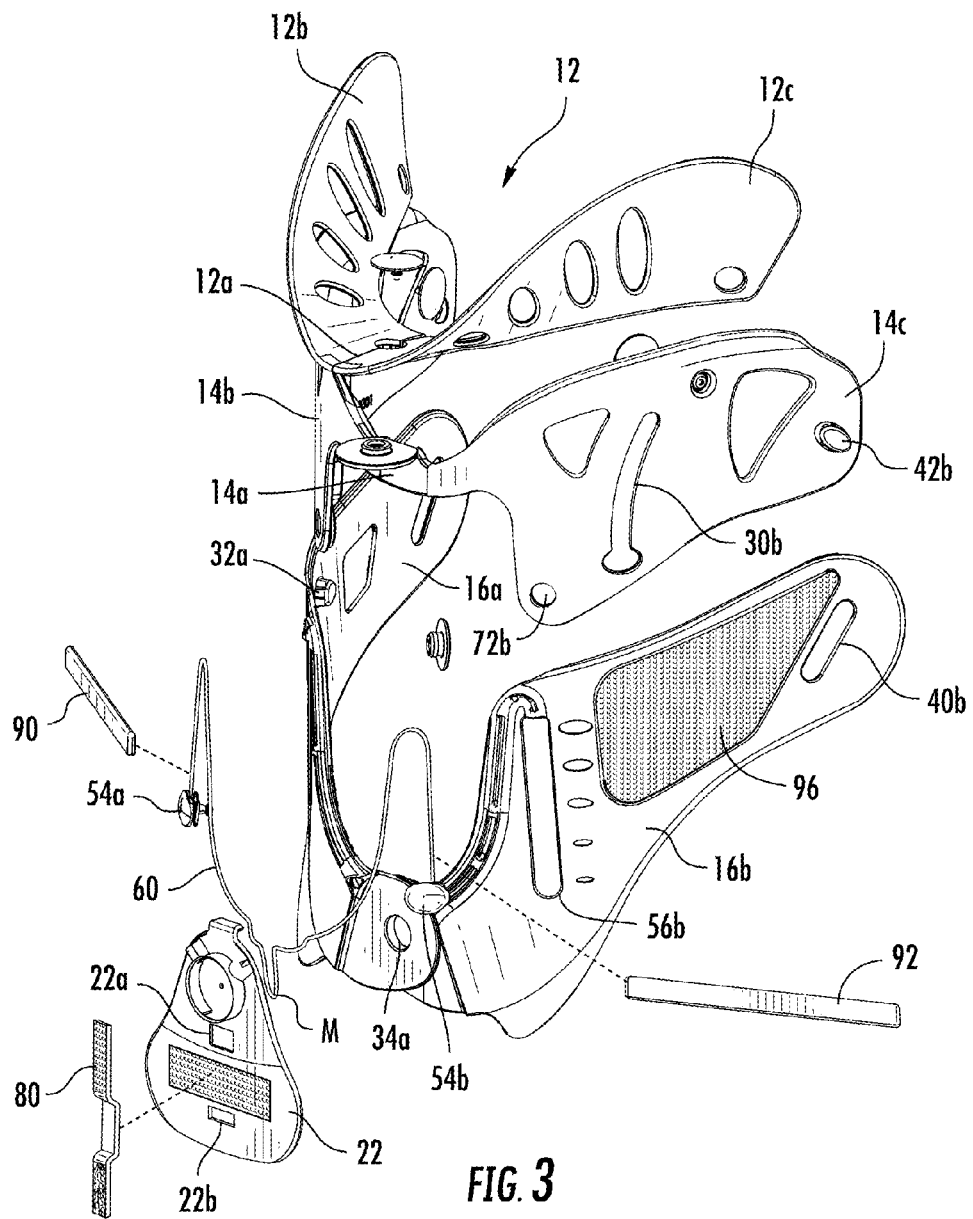
FIG. 3 shows a front exploded perspective view of the front assembly of FIG. 1.
Figure 4:
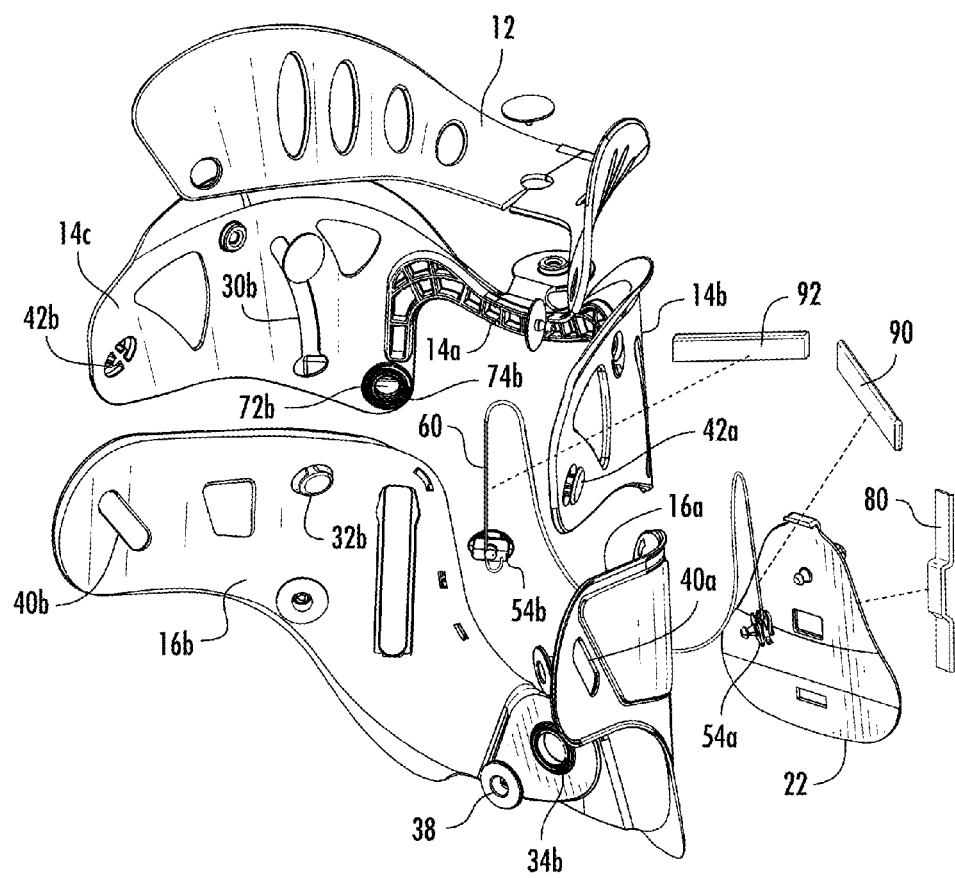
FIG. 4 is a rear exploded perspective view of the front assembly of FIG. 1.
Figure 5:
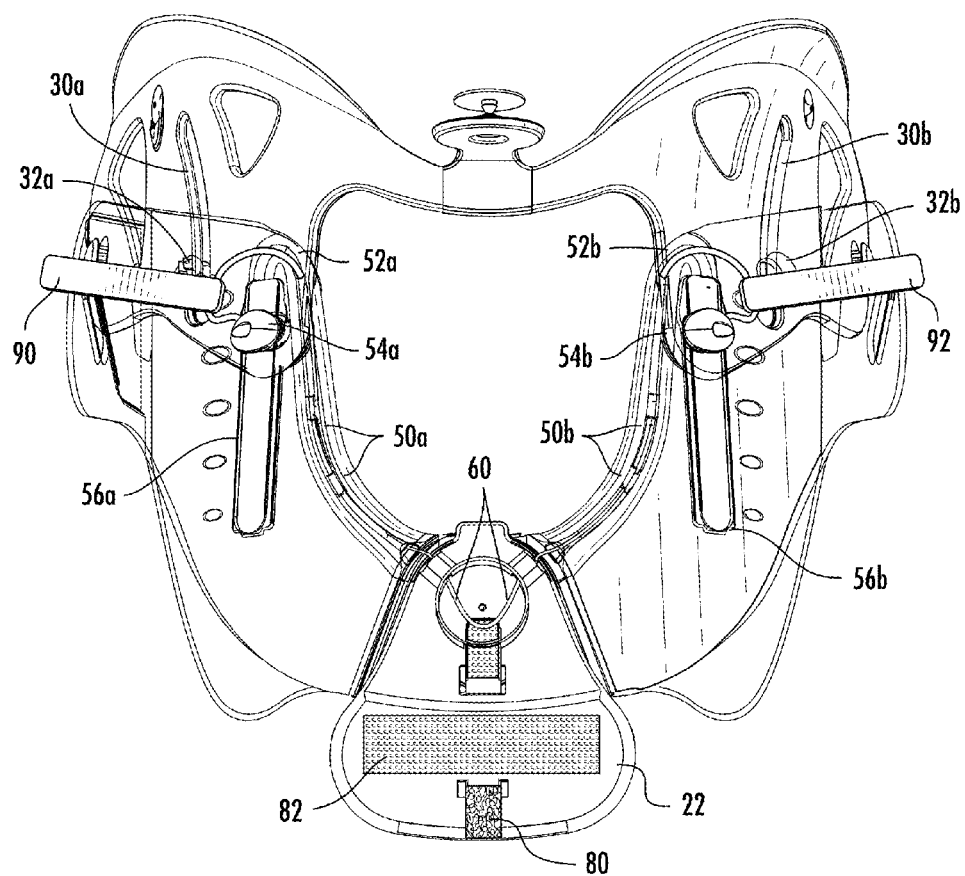
FIG. 5 is a front view of the front assembly of FIG. 1, with a body portion thereof transparent to show underlying structures.
Figure 6:
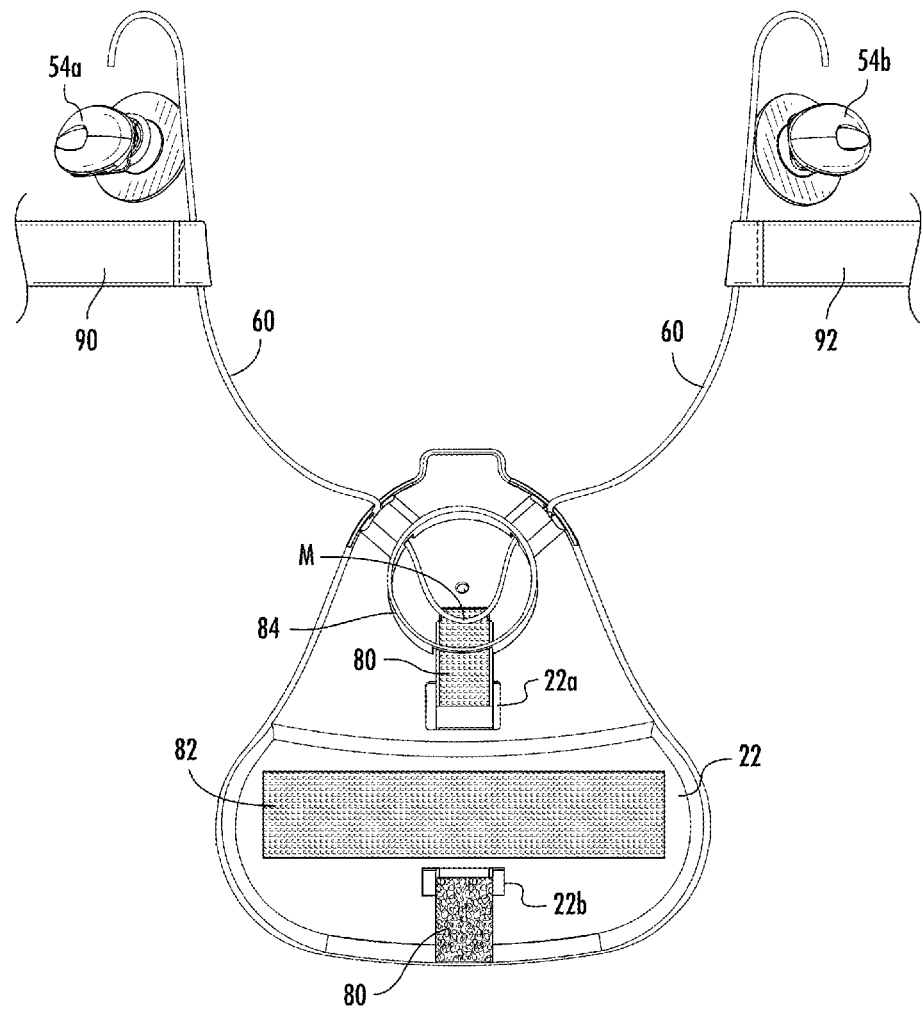
FIG. 6 shows portions of a cable adjustment system utilized on the front assembly of FIG. 1.
Figure 7:
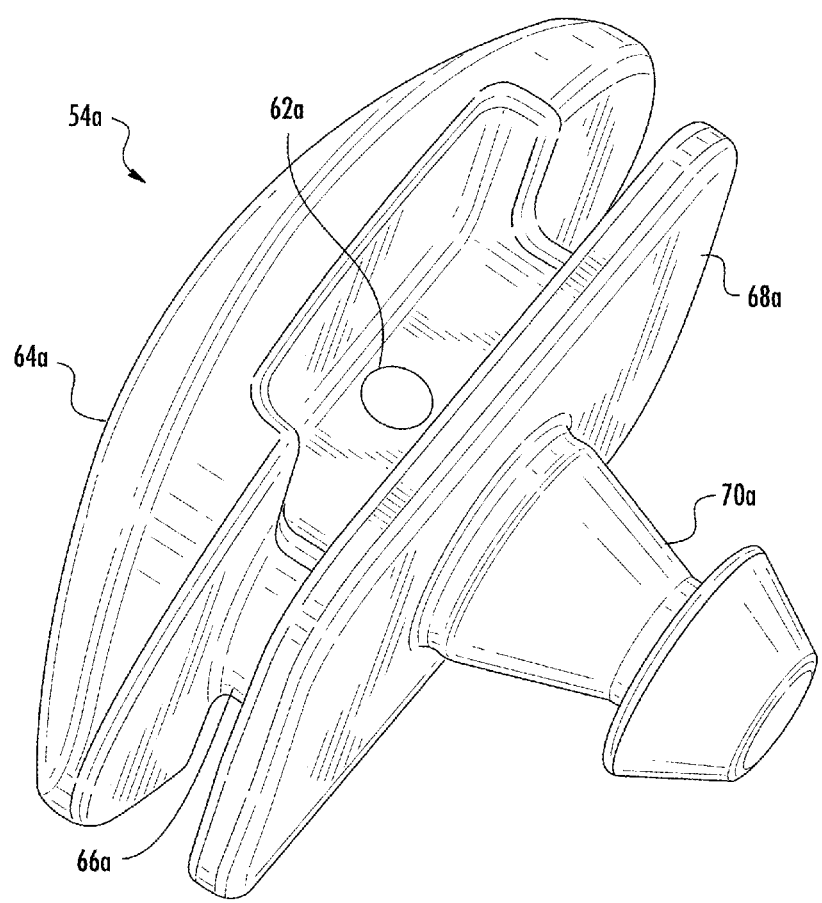
FIGS. 7 and 8 show a cable stop component of the front assembly of FIG. 1.
Figure 8:
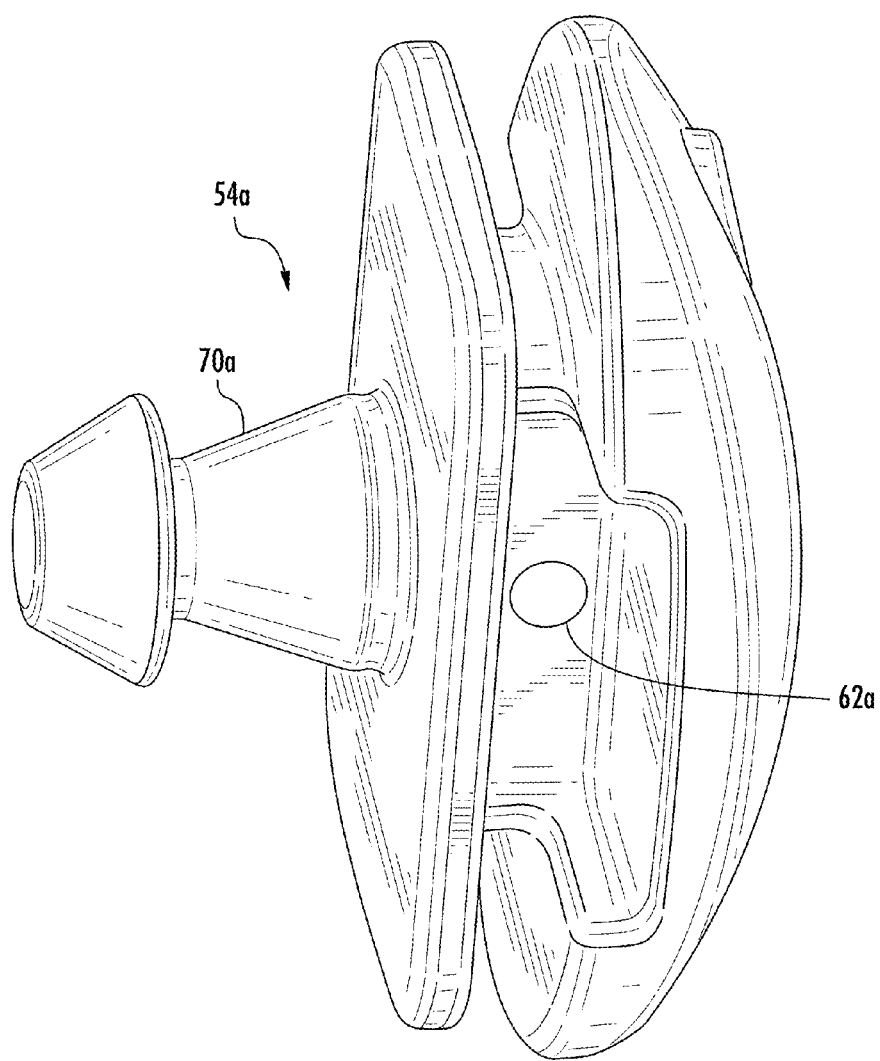
Figure 9:
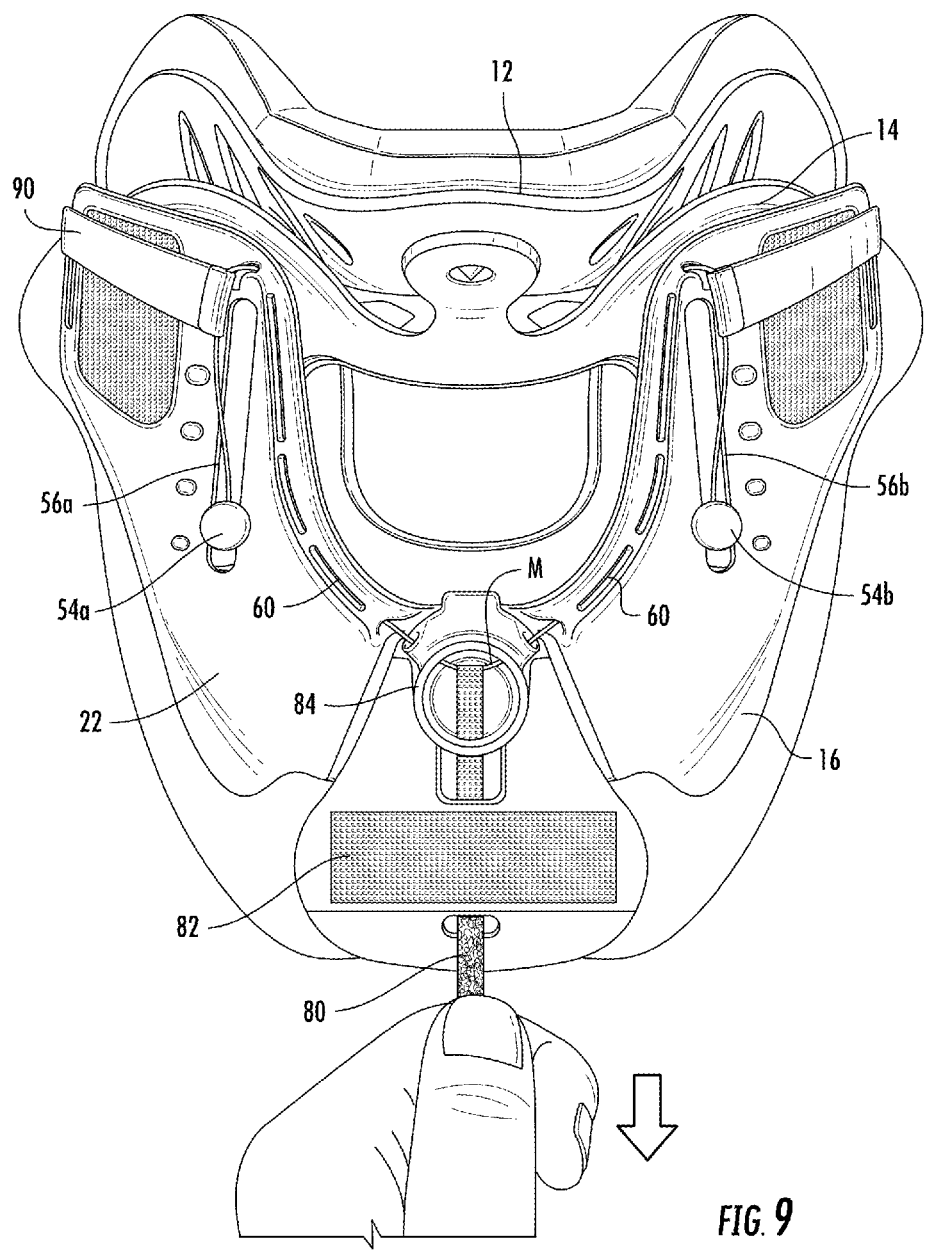
FIGS. 9-11 show use of the cable adjustment system to reposition a chin support of the front assembly of FIG. 1.

In this regard, and with reference to FIG. 9, it will be seen that the adjustment member 80 is utilized to position the midpoint M of the cable 60 at an upper location of the ring 84 on the sternal pad 22, which location of the midpoint M of the cable 60 serves to locate the cable stops 54a and 54b at their lowermost positions in the stop guides 56a and 56b. This positioning of the cable stops 54a and 54b corresponds to the chin support 12 being at its lowermost vertical height.

Figure 10:
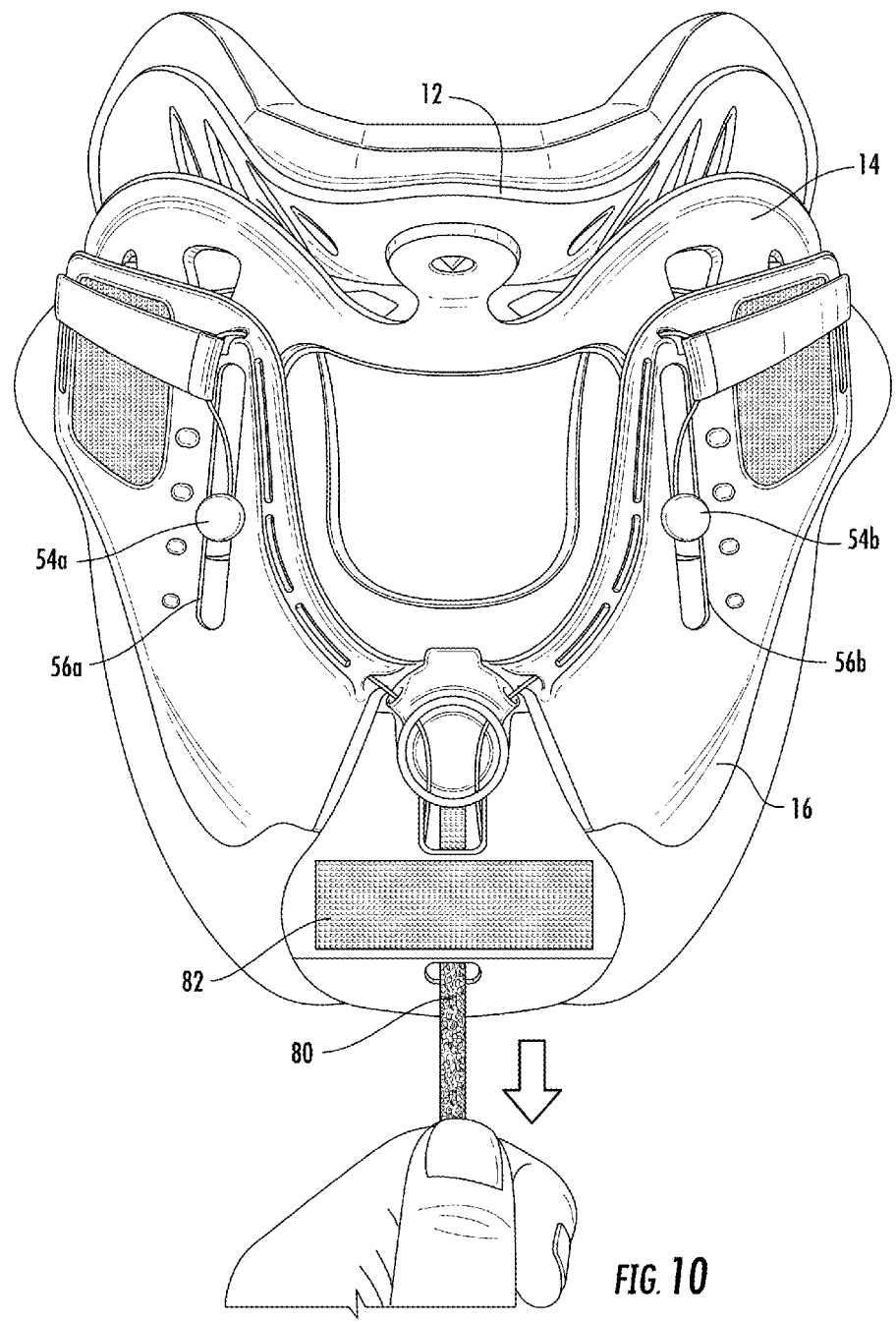

Next, with reference to FIG. 10, it will be seen that the adjustment member 80 has been manipulated to position the cable stops 54a and 54b at higher positions in the stop guides 56a and 56b. This positioning of the cable stops 54a and 54b corresponds to the chin support 12 being at greater vertical height.

Figure 11:
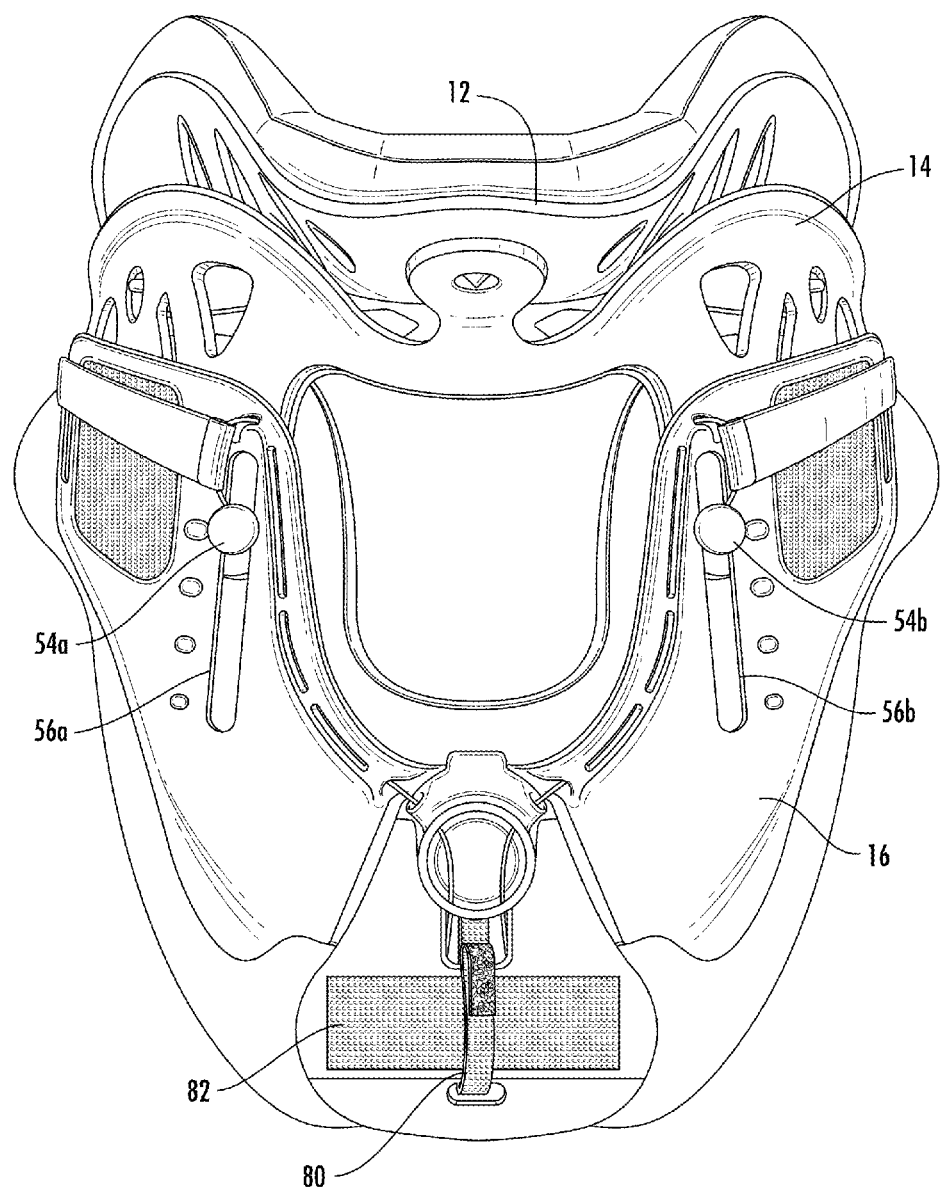

In FIG. 11, the adjustment member 80 has been further manipulated to position the cable stops 54a and 54b at their highest positions in the stop guides 56a and 56b. This positioning of the cable stops 54a and 54b corresponds to the chin support 12 being at its uppermost vertical height.

Figure 12:
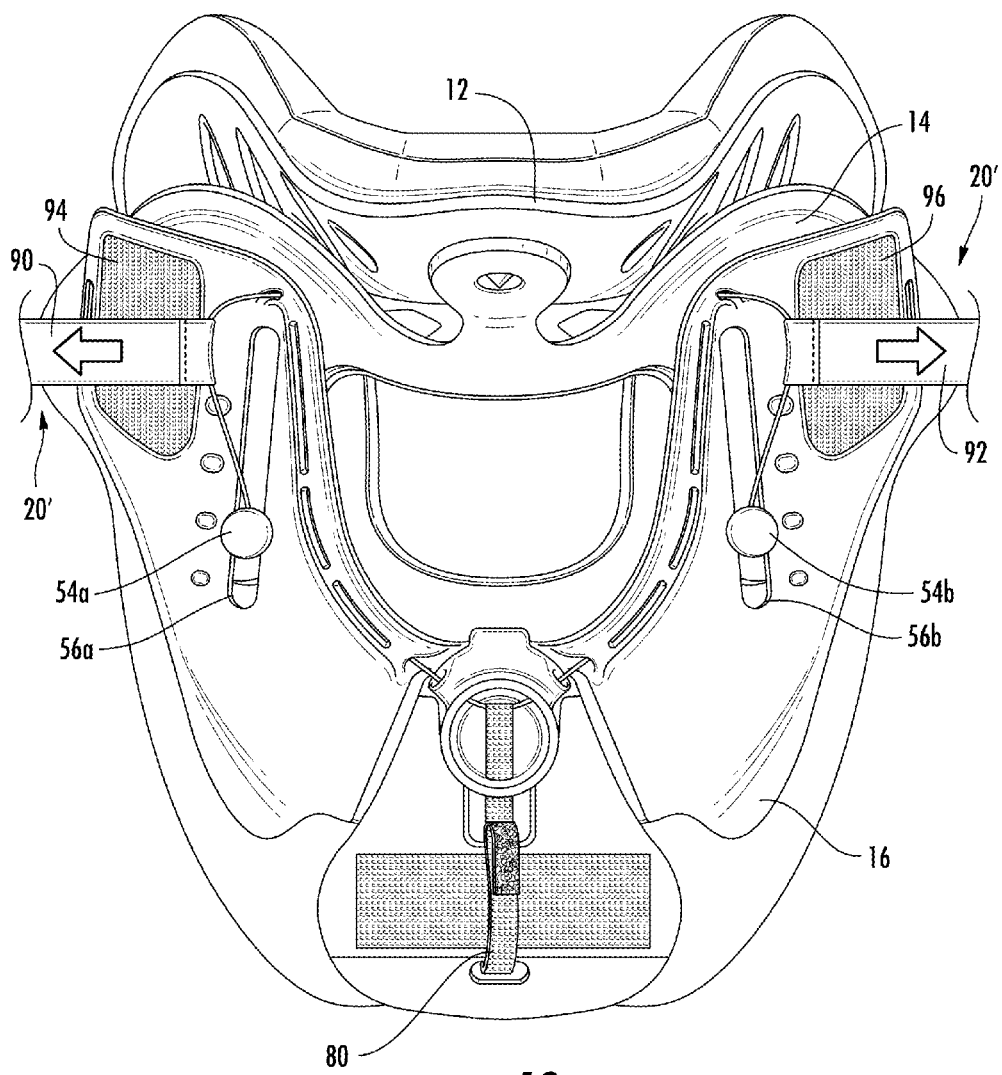
FIGS. 12-14 show additional use of the cable adjustment system to reposition a chin support of the front assembly of FIG. 1.
Figure 13:
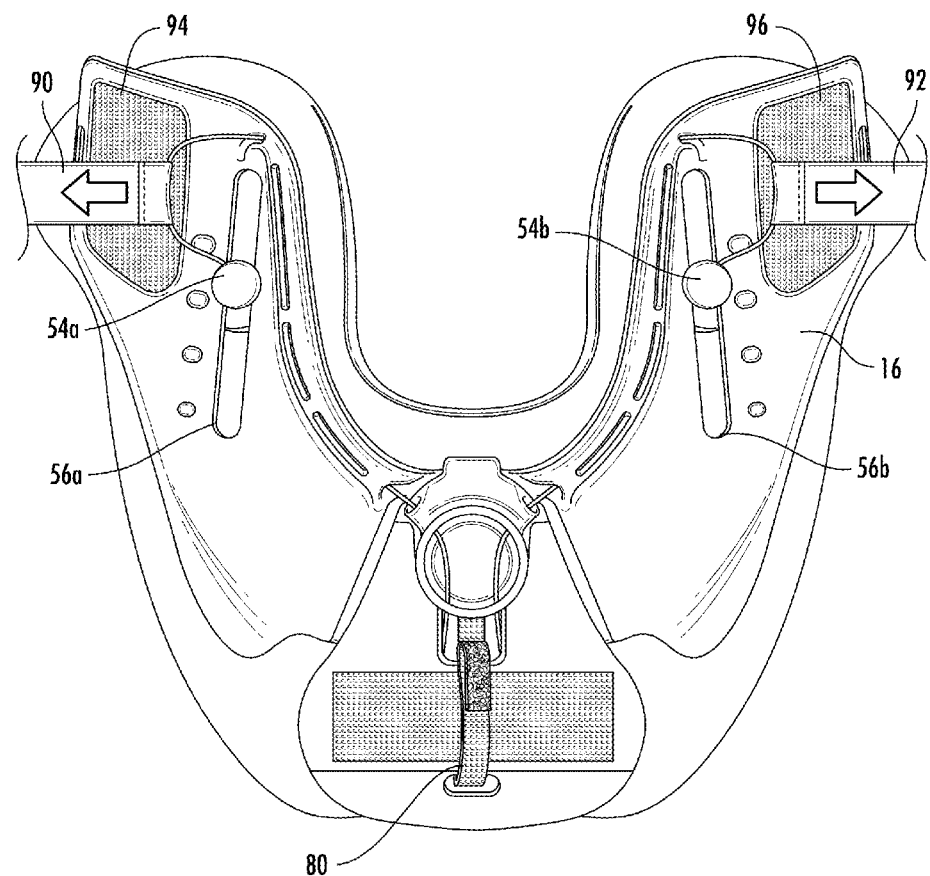
Figure 14:
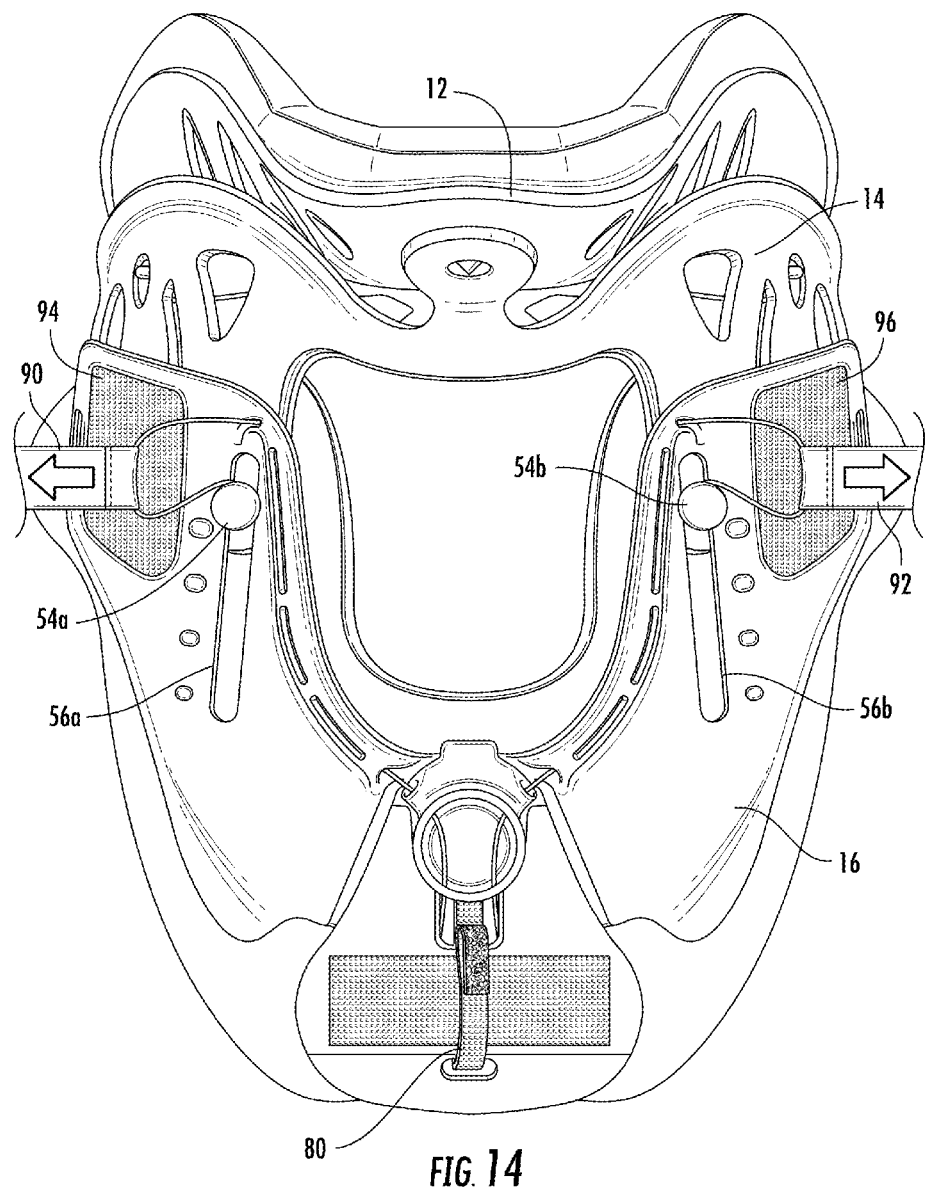

The cable adjustment system 20' is configured to include adjustment straps 90 and 92 that are connected to portions of the cable 60, as by encircling end portions of the straps about the cable and stitching to maintain the encircled relationship. The straps 90 and 92 include loop or hook material on a rear side thereof configured to matingly engage portions of hook or loop material 94 and 96, respectively. Thus, the straps 90 and 92 may be adjustably and fixedly positioned to pull on the cable 60 to adjust the positions of the cable stops 54a and 54b, as shown in FIGS. 12-14, with the position of the adjustment member 80 remaining constant and the midpoint M of the cable representing a fixed point. In this regard, it will be understood that the cable adjustment system 20' may be used in conjunction with the adjustment system 20, and both used. However, if desired, the cable adjustment system 20' may be used by itself to adjust the positions of the cables tops 54a and 54b, as depicted in FIGS. 12-14.

Alternatively, the cable 60 may be provided as two separate cables, each having a fixed point. That is, each section of the cable 60 may have an end fixed to the body 16. Also, it will be appreciated that if two separate cables are used, the cable adjustment systems 20 may be omitted. In such embodiment, it will be appreciated that the pulleys 52a and 52b may be eliminated, and the fixed points provided at locations corresponding to the locations of the pulleys 52a and 52b.

As will be appreciated, by adjusting the position of the cable stops 54a and 54b, using the adjustment system 20, the adjustment system 20', or both, the chin support 12 may be positioned at any vertical height within the range of the uppermost and lowermost positions of the cable stops 54a and 54b. Also, as the positioning systems 18a and 18b are substantially uniform in their adjustment so that the chin support remains substantially level. However, if it were desired to have an adjustment system that enabled canted or non-level adjustment, the same may be accomplished by adjusting the positions of the positioning systems 18a and 18b relative to one another or otherwise enabling different cable length adjustments.

While not required, a spring or rubber bands or other bias members may be utilized to maintain a downward bias on the cable stops 54a and 54b to minimize free play of the cable stops 54a and 54b. For example, a rubber band or the like may be attached to each of the cable stops and to a fixed point below the stops to maintain a downward bias on the cable stops.

The adjustable front assembly is assembled so that the front adjustable body portions 16a and 16b overlap at their lowermost portions and attach to one another as by plastic rivets extending through aligned apertures thereof. The adjustable body portions 16a and 16b do not move, but are adjusted by use of the cable positioning systems 18a and 18b to adjust the vertical position of the front assembly 14 relative to the adjustable body portions 16a and 16b to desirably situate the chin support 12 mounted to the front assembly.

The front assembly 14 is movably mounted to the adjustable body portions 16a and 16b by the projections of the cable stops 54a and 54b that extend through the apertures 72a and 72b and are captured by the plastic washers 74a and 74b or the like to connect the main body portion 14 and the adjustable body portions 16a and 16b. Thus, by utilizing the adjustment member 80 to move the cable stops 54a and 54b vertically within the stop guides 56a and 56b, the main body portion 14 is vertically adjusted relative to the adjustable body portions 16a and 16b commensurate with the limits of the stop guides 56a and 56b.

In addition, as other portions of the main body portion 14 and the adjustable body portions 16a and 16b are attached to one another as by fasteners, the slots 30a and 30b of the adjustable body portions 16a and 16b accommodate additional relative positioning commensurate with the vertical adjustment resulting from adjustment of the positions of the cable stops 54a and 54b of the cable positioning systems 18a and 18b. Also, the provision of the adjustable body portions 16a and 16b as separate pieces and the ability of the adjustable body portions 16b and 16b to pivot relative to one another enables improved conformity of the collar 10.

The structure of the collar 10 also advantageously enables vertical adjustment of the chin support 12 in a manner such that the orientation of the chin support 12 remains substantially constant in all vertical positions of the chin support 12. Also, the structure of the collar 10 also advantageously enables the sternal pad 22 to remain in substantial conformity with the anatomy of the patient despite adjustments of the vertical height of the chin support 12.

The foregoing description of preferred embodiments for this disclosure has been presented for purposes of illustration and description. It is not intended to be exhaustive or to limit the disclosure to the precise form disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

The invention claimed is:

1. A cervical collar having a vertically adjustable chin support, the collar comprising: a chin support adjustably connected to a collar body configured to be positioned adjacent a neck of a patient and defining a stop guide, a cable having a portion connected to an adjustment member adjustably positionable relative to the collar body for selectively adjusting the length of the cable, and a cable stop connecting between the collar body and the chin support and movably positionable along the stop guide on the collar body and a pulley located on the collar body adjacent to the elongate slot, wherein a distal portion of the cable is connected to the cable stop and the cable is trained about the pulley so that the direction of the cable is changed between the cable stop and the adjustment member, and adjustment of the length of the cable adjusts the position of the cable stop along the stop guide and adjusts the vertical position of the chin support relative to the collar body.

2. The collar of claim 1, further comprising a main collar body fixedly connected to the cable stop and connected to the chin support.

3. The collar of claim 1, wherein the stop guide comprises a slot.

4. A cervical collar having a vertically adjustable chin support, the collar comprising: a rear collar portion and a front collar assembly, the front assembly including a chin support positionable at the front of a user with the chin of the user resting in the chin support, and the rear collar portion positionable at the back of the user, with the front collar assembly and the rear collar adjustably secured together to fit the neck of the user to restrain movement of the neck, the front assembly further comprising: a main collar body connected to the chin support and an adjustable collar body connected to the main collar body, the adjustable collar body including a stop guide defined thereon, a cable having a portion connected to an adjustment member adjustably positionable on the adjustable collar body for selectively adjusting the length of the cable, and a cable stop movably positionable along the stop guide and connected to the main collar body, and a pulley located on the collar body adjacent to the stop guide, wherein a distal portion of the cable is connected to the cable stop and the cable is trained about the pulley so that the direction of the cable is changed between the cable stop and the adjustment member, and adjustment of the length of the cable adjusts the position of the cable stop along the slot and adjusts the vertical position of the chin support relative to the collar body.

5. The collar of claim 4, wherein the stop guide comprises a slot.

6. A cervical collar having a vertically adjustable chin support, the collar comprising a chin support adjustably connected to a collar body having a stop guide, an adjustment member for adjusting the length of a cable trained around a pulley located on the collar body adjacent to the cable guide and connected to a cable stop connecting between the collar body and the chin support and movably positionable along the stop guide on the collar body, wherein the length of the cable adjusts the position of the cable stop along the stop guide and adjusts the vertical position of the chin support relative to the collar body.

7. A cervical collar having a vertically adjustable chin support, the collar comprising: a chin support adjustably connected to a collar body configured to be positioned adjacent a neck of a patient and defining a stop guide, a cable having a portion connected to an adjustment member adjustably positionable relative to the collar body for selectively adjusting the length of the cable, and a cable stop connecting between the collar body and the chin support and movably positionable along the stop guide on the collar body, wherein adjustment of the length of the cable by adjusting the position of the adjustment of the adjustment member relative to the collar body adjusts the position of the cable stop along the stop guide and adjusts the vertical position of the chin support relative to the collar body.

* * * * *